(12) United States Patent
Konishi et al.

(10) Patent No.: US 9,238,087 B2
(45) Date of Patent: Jan. 19, 2016

(54) ABSORBER AND ABSORBENT ARTICLE

(75) Inventors: Takayoshi Konishi, Kanonji (JP);
Masaki Yoshida, Kanonji (JP);
Noritomo Kameda, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/007,596

(22) PCT Filed: Feb. 3, 2012

(86) PCT No.: PCT/JP2012/052536
§ 371 (c)(1),
(2), (4) Date: Feb. 4, 2014

(87) PCT Pub. No.: WO2012/132548
PCT Pub. Date: Oct. 4, 2012

(65) Prior Publication Data
US 2014/0141970 A1    May 22, 2014

(30) Foreign Application Priority Data

Mar. 25, 2011  (JP) ................................. 2011-068277

(51) Int. Cl.
*B01J 20/00* (2006.01)
*A61L 15/28* (2006.01)
*A61F 13/53* (2006.01)

(52) U.S. Cl.
CPC .................. *A61L 15/28* (2013.01); *A61F 13/53* (2013.01); *A61F 2013/530058* (2013.01); *A61F 2013/530364* (2013.01); *A61F 2013/530372* (2013.01)

(58) Field of Classification Search
CPC .................................. B01J 20/00; B01J 20/22
USPC ............................................................. 502/404
See application file for complete search history.

(56) References Cited

U.S. PATENT DOCUMENTS

| | | |
|---|---|---|
| 4,468,428 A | 8/1984 | Early et al. |
| 5,374,260 A | 12/1994 | Lemay et al. |
| 5,466,232 A | 11/1995 | Cadieux et al. |
| 5,797,894 A | 8/1998 | Cadieux et al. |
| 6,362,389 B1 | 3/2002 | McDowall et al. |
| 2003/0120232 A1 | 6/2003 | Ishikawa et al. |
| 2006/0224136 A1 | 10/2006 | Martinez |

FOREIGN PATENT DOCUMENTS

| | | |
|---|---|---|
| EP | 1961850 A1 | 8/2008 |
| JP | 55-133249 A | 10/1980 |
| JP | 2-168949 A | 6/1990 |
| JP | 2003-135524 A | 5/2003 |
| JP | 2004-19058 A | 1/2004 |
| JP | 2004-019058 A | 1/2004 |
| JP | 2007-319170 A | 12/2007 |
| WO | 0027625 A2 | 5/2000 |

OTHER PUBLICATIONS

International Search Report corresponding to PCT/JP2012/052536 Search Report dated May 1, 2012.

*Primary Examiner* — Edward Johnson
(74) *Attorney, Agent, or Firm* — Hauptman Ham, LLP

(57) ABSTRACT

An absorber containing non-wood pulp with the settling velocity in water between 2 and 5 seconds, the mean fiber size of 8 to 25 μm, the apparent bulk density of 0.04 to 0.07 g/cm³, and the absorption for 0.9% physiological saline of at least 20-fold with respect to the pulp mass. The absorber has a thickness change of at least 600%, as the thickness after having absorbed 0.9% physiological saline with respect to the thickness before absorbing 0.9% physiological saline. When addition of 80 mL of 0.9% physiological saline to the absorbent article over a period of 10 seconds is performed three times every 10 minutes and the absorption rate of the absorbent article for each of the three times is evaluated as the time from addition of the 0.9% physiological saline until complete absorption, the absorption rate for each of the three times is not greater than 20 seconds.

7 Claims, 5 Drawing Sheets

(a)

(b)

(a)

(b)

(c)

ABSORBER AND ABSORBENT ARTICLE

RELATED APPLICATIONS

The present application is a National Phase of International Application Number PCT/JP2012/052536, filed Feb. 3, 2012, and claims priority from Japanese Application Number 2011-068277, filed Mar. 25, 2011.

TECHNICAL FIELD

The invention relates to an absorber containing non-wood pulp, and to an absorbent article comprising the absorber.

BACKGROUND ART

Pulp derived from non-wood materials (non-wood pulp) has been used in the past as material for disposable absorbers to be used in diapers and sanitary articles. Bagasse, which consists of the hulls obtained after squeezing juice from sugarcane stems, has been particularly noted as a material for absorbers (PTL 1, for example). By blending pith-containing bagasse pulp and wood pulp, which differ from each other in bulk density, in a prescribed ratio, and thereby adjusting the bulk density, the water retention of the absorber is increased during pressing and compaction.

CITATION LIST

Patent Literature

[PTL 1] Japanese Unexamined Patent Publication No. S55-133249

DISCLOSURE OF THE INVENTION

Technical Problem

However, absorbers containing non-wood pulp have been desired, that have even higher absorption efficiency than the absorber described in PTL 1 that contains bagasse pulp. It is an object of the present invention to provide an absorber containing non-wood pulp and having high absorption efficiency, as well as an absorbent article containing the absorber.

Solution to Problem

In order to solve the aforementioned problem, the invention has the following feature(s).

Specifically, the invention relates to an absorber containing non-wood pulp, wherein the settling velocity of the non-wood pulp in water is between 2 seconds and 5 seconds.

The invention also relates to an absorber containing non-wood pulp, wherein the mean fiber size of the non-wood pulp is 8 to 25 μm, the apparent bulk density of the non-wood pulp is 0.04 to 0.07 g/cm$^3$, and the absorption of the non-wood pulp for 0.9% physiological saline is at least 20 times the mass of the pulp.

The invention also relates to an absorbent article comprising the absorber described above.

The invention also relates to an absorbent article comprising an absorber containing non-wood pulp and SAP, the absorber having a thickness change of at least 600%, as the thickness after having absorbed 0.9% physiological saline with respect to the thickness before absorbing 0.9% physiological saline.

The invention also relates to an absorbent article comprising an absorber containing non-wood pulp and SAP, wherein when addition of 80 mL of 0.9% physiological saline to the absorbent article over a period of 10 seconds is performed three times every 10 minutes and the absorption rate of the absorbent article for each of the three times is evaluated as the time from addition of the 0.9% physiological saline until complete absorption, the absorption rate for each of the three times is not greater than 20 seconds.

Effect of the Invention

According to the invention, it is possible to obtain an absorber and absorbent article with high absorption efficiency.

DESCRIPTION OF EMBODIMENTS

Figure 1:
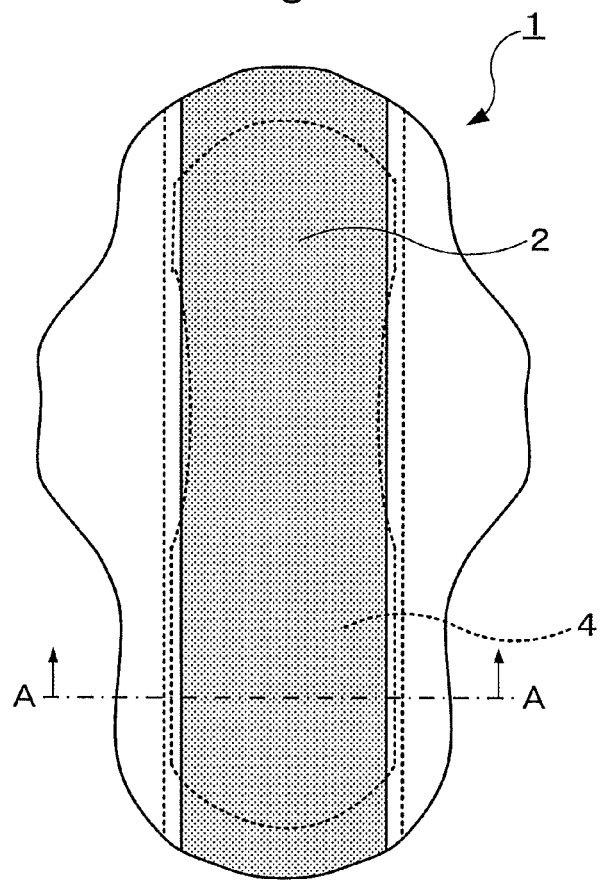
FIG. 1 is a plan view of an absorbent article according to an embodiment of the invention.
Figure 2:
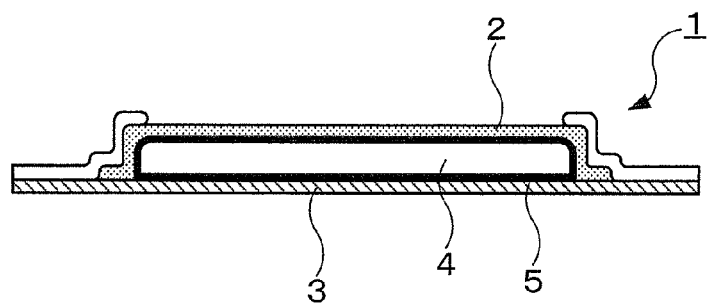
FIG. 2 is a cross-sectional view of the absorbent article of FIG. 1 along A-A.

A sanitary napkin will now be used as an example of an absorbent article according to an embodiment of the absorbent article of the invention, for explanation. FIG. 1 is a plan view of an absorbent article 1 according to an embodiment of the invention, and FIG. 2 is a cross-sectional view of the absorbent article 1 of FIG. 1 along A-A. As shown in FIG. 1 and FIG. 2, the absorbent article 1 has a liquid-permeable front sheet 2, a liquid-impermeable leakproof sheet 3, an absorber 4 situated between the front sheet 2 and the leakproof sheet 3, and a tissue 5 covering the absorber 4. A second sheet may also be situated between the front sheet 2 and the absorber 4. In this case, a nonwoven fabric with higher density than the front sheet 2 is preferably used as the second sheet, to aid absorption of body fluid from the front sheet 2.

The front sheet 2 is a liquid-permeable sheet that is permeable to body fluids, and it is provided on the front side that contacts with skin of the user, in order to improve the feel on the skin when the user wears the absorbent article 1. Thus, the front sheet 2 preferably has a function of producing a satisfactory feel on the skin. For example, the front sheet 2 may be formed by thin fibers, with a smooth front side and a high degree of freedom against deformation.

A nonwoven fabric is usually used as the front sheet 2. It may be formed by an air-through method using a known carded web. A method for producing a nonwoven fabric to be used for the front sheet 2 is not limited to the aforementioned air-through method, and for example, a nonwoven fabric may be produced by a needle punching or spunlace method wherein a fiber web is entangled to form a stable sheet, a binder bonding or thermal bonding method wherein a web is anchored by bonding the fibers or melting the fibers themselves, a spunbond method wherein sealing is accomplished using filament fibers, or a wet method involving sheet formation by paper-making.

The fibers to be used in the nonwoven fabric of the front sheet 2 are composed of, for example, linear low-density polyethylene (LLDPE), low-density polyethylene (LDPE), medium-density polyethylene (MDPE), high-density polyethylene (HDPE), polypropylene, polybutylene and copolymers composed mainly thereof, ethylene-vinyl acetate copolymer (EVA), ethylene-ethyl acrylate copolymer (EEA), ethylene-acrylic acid copolymer (EAA), polyolefin-based resins such as ionomer resins, polyester-based resins such as polyethylene terephthalate (PET), polybutylene terephthalate (PBT), polytrimethylene terephthalate (PTT) and polylactic acid, and polyamide-based resins such as nylon, as well as mixtures of the foregoing.

The leakproof sheet 3 is a liquid-impermeable sheet that is not permeable to body fluids, and it is provided so that discharged body fluids do not leak to the outside. The material of the leakproof sheet 3 is not particularly restricted so long as it is a material through which discharged body fluids do not permeate. For example, a waterproof treated nonwoven fabric, a plastic film made of polyethylene or the like, or a composite material of a nonwoven fabric and a plastic film, may be used as the leakproof sheet 3.

The absorber 4 has the function of absorbing and retaining discharged body fluid. The absorbing material to be used for the absorber 4 is preferably a mixture of pulp obtained from a material other than wood (hereunder referred to as "non-wood pulp") and a super-absorbent polymer (SAP). So long as it contains non-wood pulp, the absorbing material used in the absorber 4 may be a mixture of a non-SAP absorbing material and non-wood pulp, or non-wood pulp alone.

Non-wood pulp is pulp other than wood pulp obtained from a plant material, and non-wood pulp includes, for example, linter pulp, Manila hemp, kenaf, esparto grass, straw, bamboo or banana stem. The non-wood pulp to be used for the absorber 4 is preferably abaca pulp made from Manila hemp, and in particular a portion near the core of Manila hemp or a portion between the core and hull of Manila hemp, or banana pulp made from banana stem.

Figure 6:
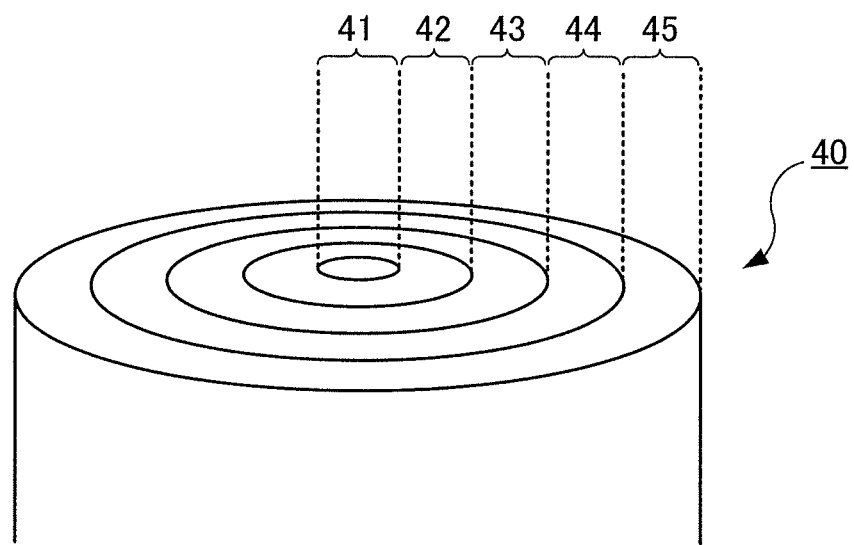
FIG. 6 is a diagram for illustration of the cross-sectional structure of Manila hemp.

The portion near the core of Manila hemp and the portion between the core and the hull of Manila hemp will now be explained with reference to FIG. 6. As shown in FIG. 6, the cross-sectional structure of the Manila hemp 40 is classified as the core 41, the portion near the core 42, the intermediate portion 43, the portion adjacent to the outside 44 and the outside 45, of Manila hemp 40. The phrase "portion near the core of Manila hemp" as used herein corresponds to the portion near the core 42 and the intermediate portion 43 of Manila hemp 40, and the "portion between the core and hull of Manila hemp" corresponds to the portion adjacent to the outside 44 of Manila hemp 40.

Abaca fiber formed from Manila hemp is classified by the portion of the Manila hemp starting material. Specifically, abaca fiber is classified as whether the starting material portion is the core 41, the portion near the core 42, the intermediate portion 43, the portion adjacent to the outside 44 or the outside 45 of Manila hemp 40. For example, abaca fiber is classified as special grade AD, EF, S2 or S3, depending on the portion that is the Manila hemp starting material. AD represents abaca fiber made from the portion near the core 42 of Manila hemp 40. AD abaca fiber is pure white fiber with gloss. EF represents abaca fiber made from the intermediate portion 43 of Manila hemp 40. EF abaca fiber is fiber from the soft pure fiber center portion, and is light ivory-colored. S2 represents abaca fiber made from the portion adjacent to the outside 44 of Manila hemp 40. S2 abaca fiber is pale yellow-colored or light-violet colored. S3 represents abaca fiber made from the outside 45 of Manila hemp 40. S3 abaca fiber is dark-red or violet-colored, and is mainly used in rope.

Abaca fiber can also be classified as special grade I, G or H, depending on the portion of the Manila hemp starting material. I represents abaca fiber made from the intermediate portion 43 of Manila hemp 40. I abaca fiber is pale yellow-colored. G represents abaca fiber made from the intermediate portion 43 of Manila hemp 40. G represents abaca fiber made from the portion adjacent to the outside 44 of Manila hemp 40. G abaca fiber is dull, dark white-colored, and tends to form bundles. H represents abaca fiber made from the outside 45 of Manila hemp 40. H abaca fiber is nearly black, dark brown-colored, and is mainly used in rope.

Abaca fiber can also be classified as special grade JK or M1, depending on the portion of the Manila hemp starting material. JK represents abaca fiber made from the portion adjacent to the outside 44 of Manila hemp 40. JK abaca fiber is tan or light-green colored, and is used mainly as pulp. M1 represents abaca fiber made from the outside 45 of Manila hemp 40. M1 abaca fiber is dark brown to black fiber, and is mainly used in rope.

Abaca fiber from the "portion near the core of Manila hemp" corresponds to abaca fiber AD, EF or I, and abaca fiber from the "portion between the core and hull of Manila hemp" corresponds to abaca fiber S2, G or JK. Abaca fiber from the hull corresponds to abaca fiber S3, H or M1.

The mean fiber size of the non-wood pulp to be used in the absorber 4 is preferably 8 µm to 25 µm and more preferably 10 µm to 20 µm. This increases the number of fibers per unit volume in the absorber 4, allowing the absorber 4 to be easily increased in thickness and the apparent bulk density to be lowered. Thus, the volume required to store absorbed user body fluids will be more easily ensured in the absorber 4. Also, since the specific surface area and the void volume between fibers of the non-wood pulp are increased, it is possible to increase the amount of absorption by the absorber 4. Furthermore, since the distance between fibers of the non-wood pulp is reduced, the force of drawing body fluids by capillary movement of the non-wood pulp is increased. In addition, tangling occurs more readily between the fibers of the non-wood pulp and between the non-wood pulp fibers and SAP, so that the absorber does not disintegrate and the shape of the absorber can be maintained, even with reduced weight and thinning of the absorber. If the mean fiber size of the non-wood pulp is smaller than 8 µm, it will be difficult to maintain the hollow structure, and bulk maintenance can potentially become impaired. If the mean fiber size of the non-wood pulp is larger than 25 µm, the effect described above may be lessened. When non-wood pulp is mixed with SAP, the non-wood pulp fibers tend to intervene between the SAP particles, thus allowing gel blocking to be inhibited.

The lignin content of the non-wood pulp used in the absorber 4 is preferably not greater than 0.5 mass % and more preferably not greater than 0.3 mass %. If the lignin content of the non-wood pulp used in the absorber 4 is greater than 0.5 mass %, the mean fiber size of the non-wood pulp used in the absorber 4 will be increased, the apparent bulk density of the absorber 4 will be increased, and the hydrophilicity of the non-wood pulp will be lowered, thereby potentially reducing the water absorption performance of the absorber 4.

The settling velocity in water for the non-wood pulp used in the absorber 4 is preferably between 2 seconds and 5 seconds, and more preferably between 2.5 seconds and 4 seconds. In this case, it is expected that the structure of the non-wood pulp fibers is a hollow structure, and that the non-wood pulp fibers are hydrophilic, and therefore the absorption of user body fluids by the absorber 4 increases. The settling velocity is the time from contact of a basket containing the non-wood pulp with a water surface, until settling occurs under the water surface, as measured in the following manner.

A 5.0 g portion of non-wood pulp is evenly packed into a cylindrical basket. The basket is formed of copper wire, the diameter of the copper wire being 0.4 mm. The weight of the basket is 3 g, the diameter is 50 mm and the height is 80 mm. The spacing between copper wires of the basket mesh is 20 mm. Ion-exchanged water is added until the water depth reaches 200 mm in a 2 liter beaker. The basket containing the non-wood pulp is then dropped from a height of 10 mm from the water surface, and the time from contact of the basket with the water surface until progression under the water surface is measured. The measured time is the settling velocity of the non-wood pulp.

If the structure of the non-wood pulp fibers is a hollow structure, the hollow structure will contain air, and settling of the non-wood pulp will thus be delayed. If the settling velocity of the non-wood pulp is less than 2 seconds, the porosity of the non-wood pulp fibers is low and they have a low degree of hollowness, and thus absorption of body fluids by the absorber 4 may be reduced. If the settling velocity of the non-wood pulp is greater than 5 seconds, the non-wood pulp fibers may have low hydrophilicity, and absorption of body fluids by the absorber 4 may be reduced.

The apparent bulk density of the non-wood pulp used in the absorber 4 is preferably between 0.04 g/cm$^3$ and 0.07 g/cm$^3$. This will increase the volume in the absorber 4 for storing absorbed user body fluids, and will increase absorption by the absorber 4. If the apparent bulk density of the non-wood pulp is lower than 0.04 g/cm$^3$, the absorber strength may be reduced and the shape retention may be impaired. If the apparent bulk density of the non-wood pulp is higher than 0.07 g/cm$^3$, the volume for storing absorbed user body fluids may be reduced, and absorption by the absorber 4 may be lowered.

The absorption of the non-wood pulp used in the absorber 4 for 0.9% physiological saline is preferably at least 20 times the mass of the non-wood pulp. Thus, it is possible to obtain an absorber with equivalent absorption to wood pulp while using a smaller amount of non-wood pulp than wood pulp, and to decrease the weight and reduce the thickness of the absorber. If the absorption of the non-wood pulp for 0.9% physiological saline is less than 20-fold, the absorption of the absorber using non-wood pulp will not be significantly different from the absorption of an absorber using wood pulp, and therefore the effect of using the non-wood pulp instead of wood pulp for absorption by the absorber 4 may be reduced.

A tissue 5 covers the absorber 4, to prevent disintegration and loss of integrity of the absorber 4. When the absorber 4 does not disintegrate even in the absence of the tissue 5, the absorbent article 1 does not need to have the tissue 5.

The absorbent article of the invention also encompasses absorbent articles that are to be used by animals other than humans, such as pets, in addition to absorbent articles used by humans.

EXAMPLES

The present invention will now be explained in greater detail by examples, with the understanding that these examples are in no way limitative on the invention.

For the examples and comparative examples, the mean fiber size, lignin content, settling velocity, fiber specific gravity, absorption, pressed water capacity, water capacity, absorber thickness, absorption rate, diffusion length and rewetting amount were measured in the following manner.

(Mean Fiber Size)

A Fiber Lab 3.8 Kajaani fiber length analyzer by Metso Automation Co. was used to measure approximately 20,000 fibers, and the mean fiber size was recorded.

(Lignin Content)

The lignin content of the pulp was measured according to the method of P. J. Van Soest et al. (Proc. Nutr. Soc., 32, 123 (1973)).

(Settling Velocity)

(1) A 5.0 g portion of non-wood pulp was evenly packed into a cylindrical basket. The basket was formed of copper wire, the diameter of the copper wire being 0.4 mm. The weight of the basket was 3 g, the diameter was 50 mm and the height was 80 mm. The spacing between copper wires of the basket mesh was 20 mm.

(2) Ion-exchanged water was added until the water depth reached 200 mm in a 2 liter beaker.

(3) The basket containing the non-wood pulp was dropped from a height of 10 mm from the surface of water in a 2 liter beaker, and the time from contact of the basket with the water surface until progression under the water surface was measured. The measured time was recorded as the settling velocity of the non-wood pulp.

(Fiber Specific Gravity)

The fiber specific gravity of the pulp was measured according to JIS M 8717, using a He gas comparative densitometer (manufactured by Tokyo Science Co., Ltd.).

(Apparent Bulk Density)

A 10 g portion of ground pulp was layered at 100 mm×100 mm. A 100 mm×100 mm board was placed over the layered ground pulp and a 100 g load weight was placed over it. The thickness of the layered ground pulp at 10 seconds after placement of the weight was used as the apparent bulk, and the apparent bulk density was calculated.

(Absorption, Pressed Water Capacity, Water Capacity)

(1) After placing 1000 mL of 0.9% physiological saline in a 2 L beaker, the liquid temperature was measured. The 0.9% physiological saline was prepared by placing 27.0 g of sodium chloride (extra pure reagent grade) in a 3 L beaker, and then adding ion-exchanged water to the 3 L beaker until the total amount of ion-exchanged water and sodium chloride reached 3000.0 g.

Figure 3:
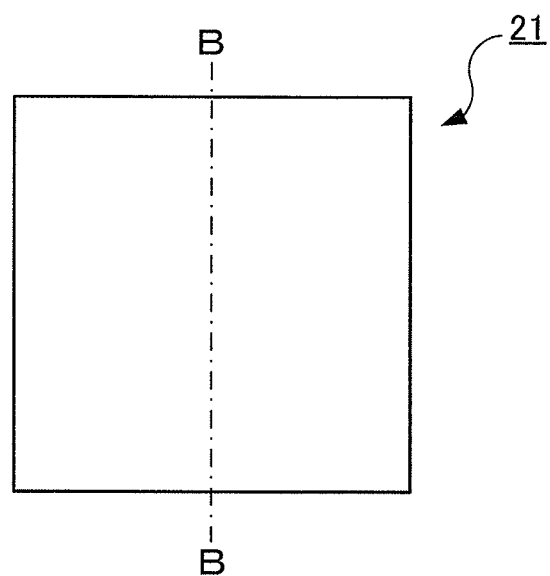
FIG. 3 is a diagram for illustration of a nylon mesh bag to be used for measurement of absorption.
Figure 3:
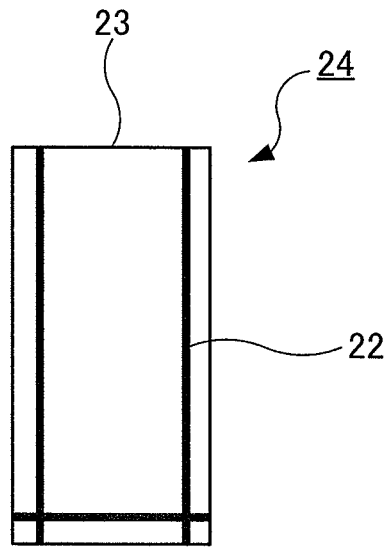

(2) A 250-mesh nylon mesh (N-NO. 250HD by NBC Industries) was cut to a size of 200 mm×200 mm and the mass (x(g)) was measured, after which it was folded at the section of the dotted line B-B shown in FIG. 3(a) to fold the nylon mesh 21 in half. As shown in FIG. 3(b), it was placed with the folded section at the right, and then heat seals 22 were formed at a location 5 mm above the bottom edge, a location 5 mm to the left of the right edge and a location 5 mm to the right of the left edge, to form a nylon mesh bag 24 with an open top edge 23. The pulverized pulp (y(g)) whose mass had been previously measured was placed in the nylon mesh bag 24, and a heat seal (not shown) was formed to close the open top edge 23 of the nylon mesh bag 24.

(3) The bag containing the ground pulp was dipped into the beaker containing the physiological saline so as to touch the bottom, and allowed to stand for 3 minutes.

(4) After standing, the bag containing the ground pulp was lifted, and allowed to stand naturally for draining, for a period of 3 minutes.

(5) The weight ($z_1$ (g)) of the bag containing the ground pulp was measured.

(6) The absorption factor was calculated by the following formula.

$$\text{Absorption (g/g)} = ((z_1 - x) - y)/y$$

(7) An acrylic board was placed on the bag containing the ground pulp that had been measured in (6), and a 100 mm×100 mm weight with a load of 3.5 kg was further placed on the acrylic board and allowed to stand for 3 minutes.

(8) The weight and acrylic board were removed, and the weight ($z_2$ (g)) of the bag containing the ground pulp was measured.

(9) The pressed water capacity was calculated by the following formula.

$$\text{Pressed water capacity (g/g)} = ((z_2 - x) - y)/y$$

(10) The bag containing the ground pulp that had been measured in (8) was dewatered with a centrifugal separator. The centrifugal separator used was a Model H130 separator by Kokusan Co., Ltd. The rotational speed of the centrifugal separator was 850 rpm (150G).

(11) The weight ($z_3$ (g)) of the dewatered bag containing the absorbing material was measured.

(12) The water capacity was calculated by the following formula.

$$\text{Water capacity (g/g)} = ((z_3 - x) - y)/y$$

(Absorber Thickness)

A thickness gauge (50 mmφ), 3 g/cm², without spring, manufactured by Peacock) was used to measure the thickness of an absorber used as the absorbent article sample. The absorber was measured at three locations, and the average value for the three measured values was recorded as the absorber thickness.

(Absorption Rate, Diffusion Length and Rewetting Amount)

(1) A cylinder with an inner diameter of 60φ) and a height of 50 mm was installed on the front sheet of the absorbent article sample, at the section corresponding to the center section of the absorber.

(2) The cylinder was injected with 80 mL of 0.9% physiological saline for 10 seconds. The 0.9% physiological saline was the same as the 0.9% physiological saline mentioned above.

(3) The time was measured from initial injection of the 0.9% physiological saline until the 0.9% physiological saline was absorbed into the absorbent article sample and disappeared from the cylinder. The measured time was recorded as the absorption rate (sec).

(4) The border of the region in which the 0.9% physiological saline diffused by 3 minutes after initial injection of the 0.9% physiological saline was traced using an oil-based ink pen. The longest diffusion length in the lengthwise direction of the absorbent article sample was recorded as the diffusion length (mm).

(5) The cylinder was removed from the absorbent article sample after 5 minutes from initial injection of the 0.9% physiological saline, and approximately 50 g of filter paper (100 mm×100 mm) whose mass had been measured beforehand was placed on the absorbent article sample, and a 3.5 kg weight (100 mm×100 mm) was placed on the filter paper.

(6) At 3 minutes after placement of the weight, the filter paper was removed and the mass of the filter paper was measured. Also, the mass of the filter paper before placement on the absorbent article sample was subtracted from the mass of the filter paper after placement, to determine the rewetting amount of the absorbent article sample.

(7) The process from injection of the 0.9% physiological saline until calculation of the rewetting amount of the absorbent article sample was carried out three times every 10 minutes, and data for the absorption rate, diffusion length and rewetting amount were recorded three times.

Example 1

Abaca BKP (AK104 by Ogura Trading Co., Ltd.) as abaca pulp obtained from the portion near the core of Manila hemp material, was pulverized into a fibrous state to prepare ground pulp of Example 1.

Example 2

Abaca BKP (AK102 by Ogura Trading Co., Ltd.) as abaca pulp obtained from the portion between the core and hull of Manila hemp material, was pulverized into a fibrous state to prepare ground pulp of Example 2.

Example 3

Banana BKP (Ogura Trading Co., Ltd.) as banana pulp obtained from banana stem material, was pulverized into a fibrous state to prepare ground pulp of Example 3.

Example 4

Figure 4:
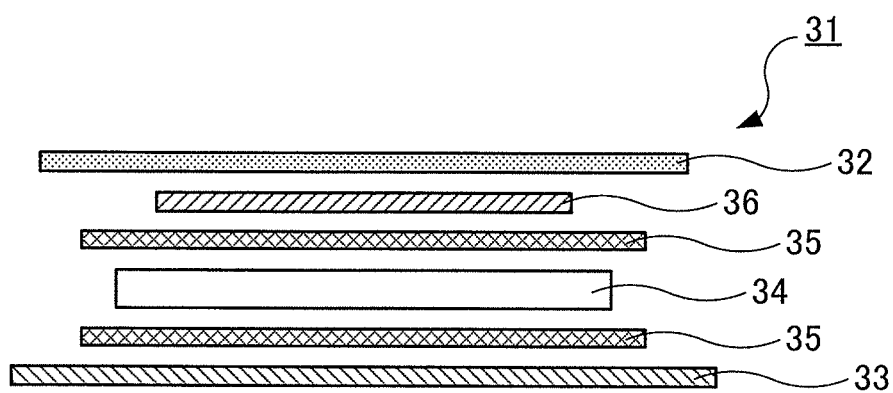
FIG. 4 is a diagram for illustration of the construction of an absorbent article sample.

An absorber was prepared comprising a uniform mixture of the ground pulp of Example 1 having a basis weight of 250 g/m² and SAP having a basis weight of 250 g/m² (AQUA KEEP SA60S by Sumitomo Seika Chemicals Co., Ltd.), to produce an absorbent article sample 31 of Example 4, which has the structure shown in FIG. 4, provided with a front sheet 32, a second sheet 36, a tissue 35, an absorber 34 and a leakproof sheet 33. The front sheet 32 was an air-through nonwoven fabric with a basis weight of 25 g/m², the second sheet 36 was an air-through nonwoven fabric with a basis weight of 20 g/m², the basis weight of the tissue 35 was 17 g/m² and the basis weight of the leakproof sheet 33 was 17 g/m². Each member was attached using a spiral hot-melt adhesive. The coating weight of the spiral hot-melt adhesive was 5 g/m².

Example 5

An absorber was prepared comprising a uniform mixture of the ground pulp of Example 1 having a basis weight of 200 g/m² and SAP having a basis weight of 250 g/m² (AQUA KEEP SA60S by Sumitomo Seika Chemicals Co., Ltd.), to produce an absorbent article sample 31 of Example 5, which has the structure shown in FIG. 4.

Example 6

An absorber was prepared comprising a uniform mixture of the ground pulp of Example 1 having a basis weight of 200 g/m² and SAP having a basis weight of 200 g/m² (AQUA KEEP SA60S by Sumitomo Seika Chemicals Co., Ltd.), to produce an absorbent article sample 31 of Example 6, which has the structure shown in FIG. 4.

Example 7

An absorber was prepared comprising a uniform mixture of the ground pulp of Example 2 having a basis weight of 250 g/m² and SAP having a basis weight of 250 g/m² (AQUA KEEP SA60S by Sumitomo Seika Chemicals Co., Ltd.), to produce an absorbent article sample 31 of Example 7, which has the structure shown in FIG. 4.

Example 8

An absorber was prepared comprising a uniform mixture of the ground pulp of Example 4 having a basis weight of 250 g/m² and SAP having a basis weight of 250 g/m² (AQUA KEEP SA60S by Sumitomo Seika Chemicals Co., Ltd.), to produce an absorbent article sample 31 of Example 3, which has the structure shown in FIG. 4.

Comparative Example 1

Ground pulp of Comparative Example 1 was produced by pulverizing wood pulp (needle bleached softwood kraft pulp (NBKP)) into a fibrous form.

Comparative Example 2

Ground pulp of Comparative Example 2 was produced by pulverizing bagasse BKP (product of Ogura Trading Co., Ltd.) into a fibrous form.

Comparative Example 3

Ground pulp of Comparative Example 3 was produced by pulverizing kenaf BKP (product of Ogura Trading Co., Ltd.) into a fibrous form.

Comparative Example 4

An absorber was prepared comprising a uniform mixture of the ground pulp of Comparative Example 1 having a basis weight of 250 g/m² and SAP having a basis weight of 250 g/m² (AQUA KEEP SA60S by Sumitomo Seika Chemicals Co., Ltd.), to produce an absorbent article sample 31 of Comparative Example 4, which has the structure shown in FIG. 4.

Comparative Example 5

An absorber was prepared comprising a uniform mixture of the ground pulp of Comparative Example 2 having a basis weight of 250 g/m² and SAP having a basis weight of 250 g/m² (AQUA KEEP SA60S by Sumitomo Seika Chemicals Co., Ltd.), to produce an absorbent article sample 31 of Comparative Example 5, which has the structure shown in FIG. 4.

Comparative Example 6

An absorber was prepared comprising a uniform mixture of the ground pulp of Comparative Example 3 having a basis weight of 250 g/m² and SAP having a basis weight of 250 g/m² (AQUA KEEP SA60S by Sumitomo Seika Chemicals Co., Ltd.), to produce an absorbent article sample 31 of Comparative Example 6, which has the structure shown in FIG. 4.

The results for the mean fiber size, lignin content, settling velocity, fiber specific gravity, apparent bulk density, absorption, pressed water capacity and water capacity for the ground pulp of Examples 1 to 3 and Comparative Examples 1 to 3 are shown in Table 1 below.

TABLE 1

|  | Type of starting material | Type of pulp | Mean fiber size (μm) | Lignin content (wt %) | Settling velocity (sec) | Fiber specific gravity (g/cm³) | Apparent bulk density (g/cm³) | Absorption (g/g) | Pressed water capacity (g/g) | Water capacity (g/g) |
|---|---|---|---|---|---|---|---|---|---|---|
| Example 1 | ABACA (near core) | ABACA BKP (AK104) | 17.9 | <0.2 | 3.30 | 1.52 | 0.054 | 25.7 | 19.0 | 7.8 |
| Example 2 | ABACA (portion between core and hull) | ABACA BKP (AK102) | 18.0 | <0.2 | 3.32 | 1.57 | 0.065 | 22.5 | 18.8 | 7.8 |
| Example 3 | Banana (stem) | Banana BKP | 12.5 | 0.3 | 2.84 | 1.46 | 0.048 | 25.9 | 13.9 | 8.2 |
| Comparative Example 1 | Softwood (Douglas fir) | Wood pulp (NBKP) | 34.5 | <0.2 | 1.04 | 1.45 | 0.083 | 16.2 | 12.0 | 8.4 |
| Comparative Example 2 | Sugar cane (bagasse) | Bagasse BKP | 12.6 | <0.2 | 1.26 | 1.50 | 0.061 | 18.8 | 16.0 | 8.3 |
| Comparative Example 3 | Kenaf (Bast) | Kenaf BKP | 12.6 | <0.2 | 1.82 | 1.50 | 0.059 | 19.2 | 12.3 | 8.4 |

The results for the properties of the absorbent article samples of Examples 4 to 8 and Comparative Examples 4 to 6, as well as the absorber thickness, absorption rate, diffusion length and rewetting amount, are shown in Table 2 below.

TABLE 2

|  | Pulp basis weight (g/m²) | SAP basis weight (g/m²) | Absorber mass (g) | Absorber thickness (before evaluation) (mm) | Absorber thickness (after evaluation) (mm) | Change in absorber thickness before and after evaluation (%) | Absorption rate 1st time (sec) | Absorption rate 2nd time (sec) |
|---|---|---|---|---|---|---|---|---|
| Example 4 | 250 | 250 | 29.4 | 3.6 | 21.5 | 606 | 11.0 | 10.6 |
| Example 5 | 200 | 250 | 27.7 | 3.0 | 18.8 | 637 | 11.9 | 12.2 |
| Example 6 | 200 | 200 | 25.3 | 2.9 | 17.8 | 614 | 11.6 | 13.6 |
| Example 7 | 250 | 250 | 29.5 | 3.6 | 20.5 | 569 | 11.5 | 12.1 |
| Example 8 | 250 | 250 | 29.3 | 3.6 | 24.5 | 681 | 10.2 | 10.8 |
| Comparative Example 4 | 250 | 250 | 29.6 | 3.6 | 13.5 | 375 | 11.3 | 14.1 |

TABLE 2-continued

| | | | | | | | |
|---|---|---|---|---|---|---|---|
| Comparative Example 5 | 250 | 250 | 29.5 | 3.5 | 17.7 | 506 | 11.4 | 14.3 |
| Comparative Example 6 | 250 | 250 | 29.4 | 3.5 | 16.2 | 463 | 11.0 | 13.8 |

| | Absorption rate 3rd time (sec) | Diffusion length 1st time (mm) | Diffusion length 2nd time (mm) | Diffusion length 3rd time (mm) | Rewetting amount 1st time (g) | Rewetting amount 2nd time (g) | Rewetting amount 3rd time (g) |
|---|---|---|---|---|---|---|---|
| Example 4 | 12.7 | 190 | 198 | 239 | 0.21 | 5.84 | 15.22 |
| Example 5 | 18.2 | 196 | 208 | 260 | 0.18 | 8.38 | 18.21 |
| Example 6 | 17.9 | 222 | 242 | 312 | 0.21 | 8.30 | 18.82 |
| Example 7 | 17.3 | 188 | 210 | 265 | 0.20 | 7.14 | 16.31 |
| Example 8 | 11.6 | 195 | 204 | 266 | 0.15 | 4.35 | 14.40 |
| Comparative Example 4 | 26.8 | 221 | 241 | 280 | 0.26 | 8.54 | 18.61 |
| Comparative Example 5 | 22.4 | 210 | 232 | 255 | 0.22 | 7.78 | 18.01 |
| Comparative Example 6 | 23.1 | 220 | 245 | 279 | 0.24 | 8.01 | 18.15 |

Each of Examples 1 to 3 had absorption for 0.9% physiological saline that was at least 20 times the mass of the pulp. Also, Each of Examples 1 to 3 had settling velocity between 2 seconds and 5 seconds. In addition, Each of Examples 1 to 3 had mean fiber sizes between 8 μm and 25 μm and apparent bulk density between 0.04 g/cm$^3$ and 0.07 g/cm$^3$.

Comparative Example 1 had a large mean fiber size of 34.5 μm, a rapid settling velocity in water of 1.04 seconds, a large apparent specific gravity of 0.083 g/cm$^3$, and a low absorption for 0.9% physiological saline of 16.2 times the pulp mass. Comparative Example 2 had a rapid settling velocity of 1.26 seconds, and a low absorption for 0.9% physiological saline of 18.8 times the pulp mass. Comparative Example 3 had a rapid settling velocity of 1.82 seconds, and a low absorption for 0.9% physiological saline of 19.2 times the pulp mass.

Figure 5:
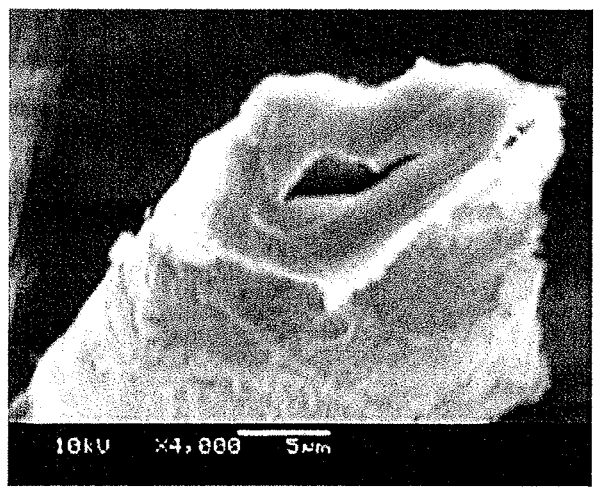
FIG. 5 is a scanning electron micrograph of a cross-section of a ground pulp fiber.
Figure 5:
Figure 5:
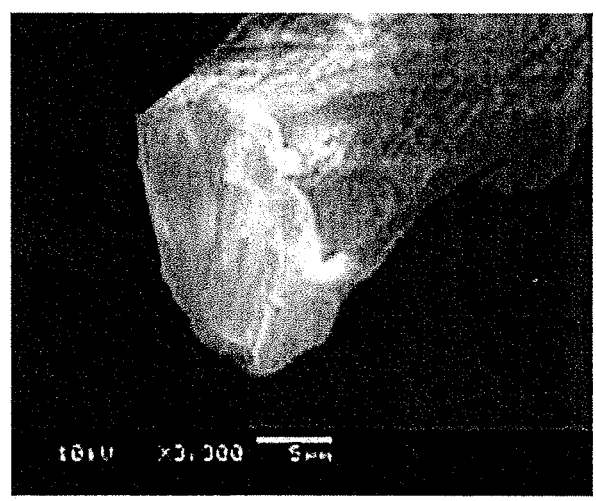

Each of Examples 1 and 2 using abaca pulp has absorption that is at least 50% higher than Comparative Example 1 using wood pulp, and therefore can absorb body fluid in at least an equivalent amount as wood pulp, with a smaller amount than wood pulp. Also, since the water capacities of Examples 1 and 2 are equal to or less than the wood pulp of Comparative Example 1, this means that when the absorber material is a mixture of pulp fiber and SAP, transfer of liquid from the pulp fiber into the SAP is satisfactory, and the repeated absorption performance is satisfactory. The properties of Examples 1 and 2, of low water capacity despite large absorption, are also exhibited by Example 3 using banana pulp. The properties of Examples 1 to 3 of low water capacity despite large absorption, are thought to be due to the hollow structure of the fibers of Examples 1 to 3. FIG. 5 shows scanning electron microscope (SEM) photographs of cross-sections of a fiber of abaca pulp, banana pulp and wood pulp, respectively. FIG. 5(a) is a SEM photograph of the cross-section of an abaca pulp fiber, FIG. 5(b) is a SEM photograph of the cross-section of a banana pulp fiber, and FIG. 5(c) is a SEM photograph of the cross-section of a wood pulp fiber. Judging by these photographs, the structures of the abaca pulp and banana pulp fibers are hollow structures. On the other hand, the structure of the wood pulp fiber which has low absorption is seen to be not a hollow structure. Abaca pulp is expected to have excellent liquid uptake into the fiber interiors, due to voids between the hollow structure fibers, and thus excellent pressed water retention. Banana pulp takes up liquid in the fiber interiors and between the fibers due to the narrowness of the fibers and the voids between fibers, and is therefore expected to have excellent diffusibility, pressed water retention and water retention. Since the pressed water capacities of Examples 1 and 2 are at least 50% higher than the wood pulp of Comparative Example 1, this means that when the absorber material is a mixture of pulp fiber and SAP, the rewetting amount of the absorber is reduced, as liquid is not released from the pulp fiber even if body pressure is applied to the absorber before liquid transfers from the pulp fiber to the SAP.

Examples 4 to 8 had high absorber thickness changes of at least 600%, before and after evaluation of the absorption rate, diffusion length and rewetting amount, as well as rapid absorption for 0.9% physiological saline, low diffusion and low rewetting amounts. For the three evaluations of the absorption rate, all three were within 20 seconds. This indicates that the absorption properties of the absorbent article sample produced using ground pulp in Examples 1 to 3 were excellent. That is, it was shown that the absorption properties were excellent with absorbent article samples using ground pulp having absorption for 0.9% physiological saline that was at least 20-fold with respect to the pulp mass. In addition, it was shown that the absorption properties were excellent with absorbent article samples using ground pulp having a settling velocity of between 2 seconds and 5 seconds. Furthermore, it was shown that the absorption properties were excellent with absorbent article samples using ground pulp having a mean fiber size of between 8 μm and 25 μm and an apparent bulk density of between 0.04 g/cm$^3$ and 0.07 g/cm$^3$.

Because of rapid transfer of liquid from pulp fiber into SAP, by which the SAP readily swells, in Examples 4 to 8 there may be expected to be a large absorber thickness change before and after evaluation of the absorption rate, diffusion length and rewetting amount. Comparative Examples 4, 5 and 6 had low absorber thickness changes of about 500% before and after evaluation of the absorption rate, diffusion length and rewetting amount. This is attributed to a lack of smooth transfer of liquid from the pulp fiber into the SAP in Comparative Examples 4, 5 and 6. Also, the absorption of 0.9% physiological saline by Comparative Examples 4, 5 and 6 was rapid for the first and second measurements, but slow for the third measurement. That is, the repeated absorption property of Comparative Example 4 was poor. Examples 6 and 7 had low rewetting amounts for the first measurement, but high rewetting amounts for the second and subsequent measurements.

Upon comparing Example 8 with Comparative Example 5 and Comparative Example 6, it was seen that by using ground pulp (Example 3) that had more excellent absorption properties than Comparative Examples 2 and 3, it was possible to obtain an absorbent article sample (Example 8) with more excellent absorption properties than Comparative Examples 5 and 6.

EXPLANATION OF SYMBOLS 1, 31 Absorbent article
2, 32 Front sheet
3, 33 Leakproof sheet
4, 34 Absorber
5, 35 Tissue
21 Nylon mesh
22 Heat seal
24 Nylon mesh bag
36 Second sheet
40 Manila hemp
41 Core
42 Portion near the core
43 Intermediate portion
44 Portion adjacent to the outside
45 Outside

The invention claimed is:

1. An absorber containing non-wood pulp, wherein
the non-wood pulp is abaca pulp made from a portion near the core of Manila hemp or a portion between the core and hull of Manila hemp, or banana pulp made from banana stem,
the mean fiber size of the non-wood pulp is 8 to 25 μm,
the apparent bulk density of the non-wood pulp is 0.04 to 0.07 g/cm$^3$,
the absorption of the non-wood pulp for 0.9% physiological saline is at least 20 times the mass of the pulp, and
the settling velocity of the non-wood pulp in water is between 2 seconds and 5 seconds.

2. The absorber according to claim 1, which further comprises SAP.

3. An absorbent article comprising the absorber according to claim 1.

4. An absorbent article comprising the absorber according to claim 2.

5. The absorbent article according to claim 4, wherein the absorber contains the non-wood pulp at a basis weight of from 200 to 250 g/m$^2$.

6. The absorbent article according to claim 4, wherein the absorber has a thickness change of at least 600%, as the thickness after having absorbed 0.9% physiological saline with respect to the thickness before absorbing 0.9% physiological saline.

7. The absorbent article according to claim 4, wherein when addition of 80 mL of 0.9% physiological saline to the absorbent article over a period of 10 seconds is performed three times every 10 minutes and the absorption rate of the absorbent article for each of the three times is evaluated as the time from addition of the 0.9% physiological saline until complete absorption, the absorption rate for each of the three times is not greater than 20 seconds.

* * * * *